US010426423B2

(12) United States Patent
Katsumata et al.

(10) Patent No.: US 10,426,423 B2
(45) Date of Patent: Oct. 1, 2019

(54) RADIOGRAPHING SYSTEM AND RADIOGRAPHING METHOD FOR REDUCING SCATTERED RADIATION COMPONENT FROM RADIOGRAPHIC IMAGE AND GENERATING LONG-SIZED IMAGE

(71) Applicant: CANON KABUSHIKI KAISHA, Tokyo (JP)

(72) Inventors: Shinya Katsumata, Kawasaki (JP); Yoshinori Hirano, Kashiwa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/482,494

(22) Filed: Apr. 7, 2017

(65) Prior Publication Data

US 2017/0296133 A1 Oct. 19, 2017

(30) Foreign Application Priority Data

Apr. 13, 2016 (JP) .................. 2016-080646

(51) Int. Cl.
*A61B 6/00* (2006.01)
*G06T 5/00* (2006.01)
*G06T 5/50* (2006.01)
*G06T 7/00* (2017.01)

(52) U.S. Cl.
CPC .............. *A61B 6/5282* (2013.01); *A61B 6/50* (2013.01); *A61B 6/5241* (2013.01); *A61B 6/5294* (2013.01); *G06T 5/003* (2013.01); *G06T 5/50* (2013.01); *G06T 7/0012* (2013.01)

(58) Field of Classification Search
None
See application file for complete search history.

(56) References Cited

U.S. PATENT DOCUMENTS

| 2016/0035451 A1* | 2/2016 | Tsuji | A61B 6/4266 378/62 |
| 2016/0287195 A1* | 10/2016 | Tagawa | A61B 6/4266 |
| 2017/0055933 A1* | 3/2017 | Kawamura | A61B 6/5282 |

FOREIGN PATENT DOCUMENTS

JP 2012040140 A 3/2012

* cited by examiner

*Primary Examiner* — Idowu O Osifade
(74) *Attorney, Agent, or Firm* — Canon U.S.A., Inc., IP Division (57) ABSTRACT

A radiographing system and a radiographing method capable of improving the image quality of a long-sized image by appropriately correcting scattered radiation are disclosed. The radiographing system includes a plurality of radiation detecting apparatuses that can detect radiation and output radiographic images, a composition processing unit configured to generate a long-sized image by composing a plurality of radiographic images acquired from the plurality of radiation detecting apparatuses, and a scattered radiation correction unit configured to perform processing for correcting scattered radiation for a radiographic image output from at least one of the plurality of radiation detecting apparatuses.

12 Claims, 6 Drawing Sheets

RADIOGRAPHING SYSTEM AND RADIOGRAPHING METHOD FOR REDUCING SCATTERED RADIATION COMPONENT FROM RADIOGRAPHIC IMAGE AND GENERATING LONG-SIZED IMAGE

BACKGROUND OF THE INVENTION

Field of the Invention

The present invention relates to a radiographing system that can perform an imaging operation with radiation and a related radiographing method.

Description of the Related Art

Recently, a long-size imaging in a wide observation region, such as imaging of a spinal cord or a lower limb of a subject or imaging of the whole body of the subject, has been performed in the medical field. As discussed in Japanese Patent Application Laid-Open No. 2012-040140, there is a conventional radiographing system that can perform a long-size imaging operation with a plurality of radiation detecting apparatuses (i.e., radiographing apparatuses) arrayed in such a manner that neighboring radiation detecting apparatuses partly overlap with each other.

The radiographing system discussed in Japanese Patent Application Laid-Open No. 2012-040140 includes a radiation generating unit that can generate radiation. When the radiographing system performs an imaging operation while partly superimposing a radiation detecting apparatus on another, scattered radiation may occur when the radiation transmits through a subject. However, the radiographing system discussed in Japanese Patent Application Laid-Open No. 2012-040140 does not include any configuration capable of solving the problem caused by the above-mentioned scattered radiation.

SUMMARY OF THE INVENTION

In view of the foregoing, in accordance with an aspect of the present invention, a radiographing system can appropriately perform scattered radiation correction and improve the image quality of a long-sized image. In accordance with another aspect of the present invention, a related radiographing method is provided.

According to another aspect of the present invention, a radiographing system includes a plurality of radiation detecting apparatuses that can detect radiation and output radiographic images, a composition processing unit configured to generate a long-sized image by composing a plurality of radiographic images acquired from the plurality of radiation detecting apparatuses, and a scattered radiation correction unit configured to perform scattered radiation correction for image data output from at least one of the plurality of radiation detecting apparatuses.

Further features of the present invention will become apparent from the following description of example embodiments with reference to the attached drawings.

DESCRIPTION OF THE EMBODIMENTS

Various example embodiments of the present invention will be described in detail below with reference to attached drawings.

Figure 1:
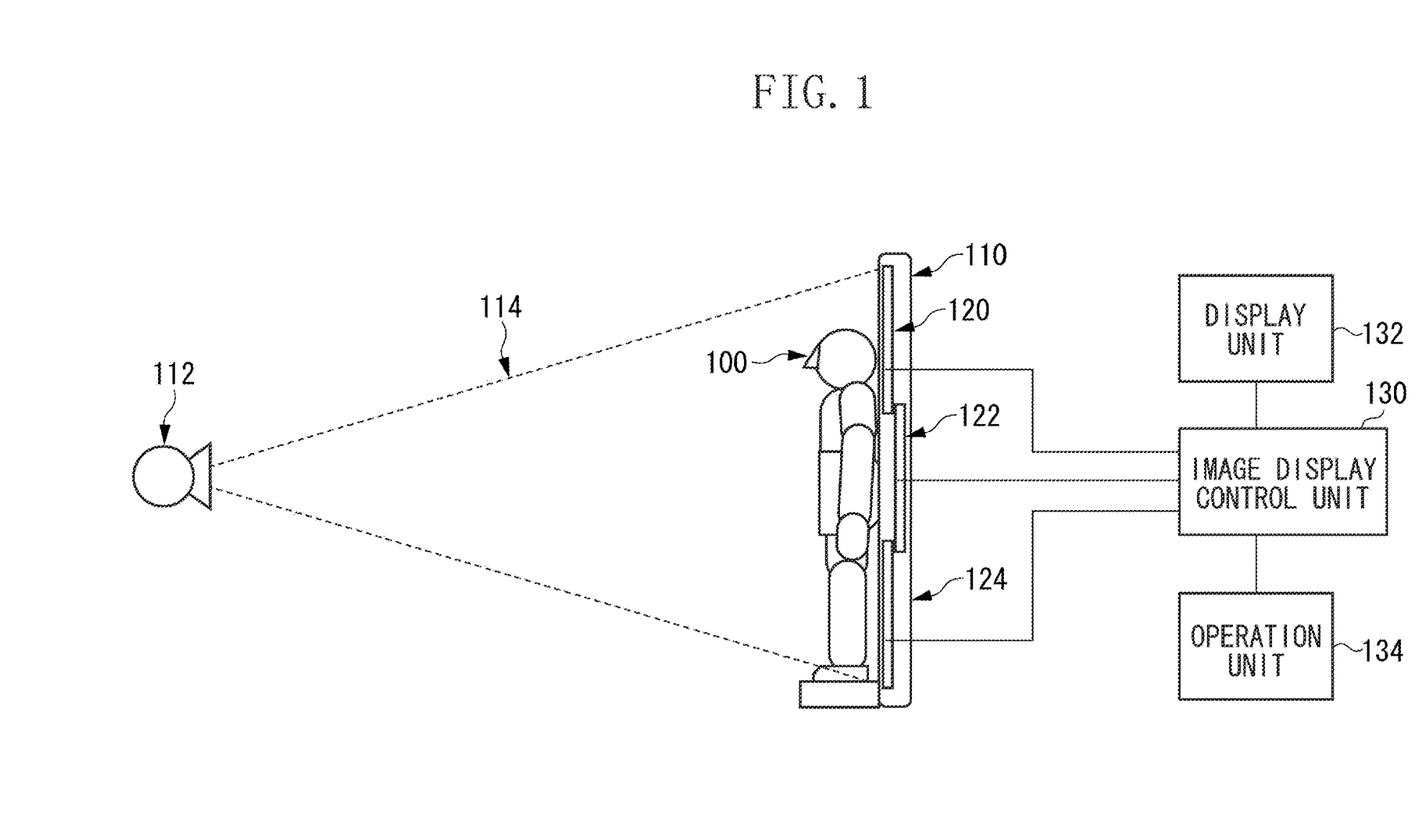
FIG. 1 illustrates a schematic configuration of a radiographing system according to an example embodiment of the present invention.

A first example embodiment will be described in detail below. FIG. 1 illustrates a schematic configuration of a radiographing system according to an example embodiment of the present invention, which includes a plurality of radiation detecting apparatuses arrayed in such a way as to perform a long-size imaging operation.

The radiographing system includes a radiation generating unit 112 that can generate radiation. The radiation generating unit 112 can emit radiation within an irradiation range 114. The radiation generating unit 112 is supported by a support member (not illustrated) installed on a floor or a ceiling. A diaphragm (not illustrated), which can shield at least a part of the radiation, is installed on an irradiation surface of the radiation generating unit 112. An operator can control the diaphragm (i.e., the device capable of shielding radioactive ray) to set the irradiation range 114 within which the radiation generating unit 112 can emit the radiation.

The radiographing system includes a plurality of radiation detecting apparatuses 120, 122, and 124. However, the radiation detecting apparatuses 120, 122, and 124 illustrated in the present example embodiment are mere examples. The total number of radiation detecting apparatuses included in the radiographing system can be reduced to two or can be increased to four or more. The plurality of radiation detecting apparatuses 120, 122, and 124 can detect radiation having passed through a subject 100 and can output image data based on the detected radiation. In the following description, the image data may be referred to as radiographic images.

More specifically, the plurality of radiation detecting apparatuses 120, 122, and 124 can detect the radiation having passed through the subject as electric charges corresponding to the amount of transmitted radiation dose. For example, a direct conversion type sensor that uses an a-Se element capable of directly converting radiation into electric charges or an indirect-type sensor that uses a scintillator (e.g., CsI) and a photoelectric conversion element (e.g., a-Si) is a practical sensor employable as the radiation detecting apparatus. Further, the plurality of radiation detecting apparatuses 120, 122, and 124 can perform A/D conversion processing to generate image data from the detected electric charges and can output the generated image data to an image display control unit 130.

The above-mentioned plurality of radiation detecting apparatuses are accommodated or housed in a photography platform 110. The photography platform 110 is a rectangular casing, which has a hollow inner space. Further, the photography platform 110 can fixedly hold the plurality of radiation detecting apparatuses 120, 122, and 124.

As illustrated in FIG. 1, the photography platform 110 stands upright on the floor in an installed state. The subject 100 is located along a longitudinal direction of the photography platform 110. In this respect, the photography platform 110 has a support function of supporting the subject 100.

According to the installed state of the photography platform 110 illustrated in FIG. 1, the longitudinal direction of the photography platform 110 is a vertical direction and the photography platform 110 stands upright on the floor. As another example, the photography platform 110 can be installed differently in such a manner that the longitudinal direction of the photography platform 110 becomes a horizontal direction. In this case, the photography platform 110 can be arranged in parallel with the floor.

The first radiation detecting apparatus 120, the second radiation detecting apparatus 122, and the third radiation detecting apparatus 124 are disposed sequentially along the longitudinal direction of the photography platform 110. In this case, neighboring radiation detecting apparatuses are arranged in a partly overlapping manner in the state where the radiation detecting apparatuses are disposed sequentially on the photography platform 110. For example, as illustrated in FIG. 1, the first radiation detecting apparatus 120 and the second radiation detecting apparatus 122 spatially overlap with each other at end portions thereof. In this case, a photographable region of the first radiation detecting apparatus 120 and a photographable region of the second radiation detecting apparatus 122 partly overlap with each other. Similarly, the second radiation detecting apparatus 122 and the third radiation detecting apparatus 124 spatially overlap with each other at end portions thereof. In this case, the photographable region of the second radiation detecting apparatus 122 and a photographable region of the third radiation detecting apparatus 124 partly overlap with each other. Further, the second radiation detecting apparatus 122 is disposed on the back side of the first radiation detecting apparatus 120 and the third radiation detecting apparatus 124. More specifically, the distance from the radiation generating unit 112 to the second radiation detecting apparatus 122 is longer compared to the distance from the radiation generating unit 112 to the first and third radiation detecting apparatuses 120 and 124.

Further, the radiographing system includes the image display control unit 130, a display unit 132, and an operation unit 134. The image display control unit 130 can perform image processing on the image data output from respective radiation detecting apparatuses and can generate an image as an output of the image processing. The display unit 132 can display the image generated by the image display control unit 130. The operation unit 134 enables an operator to enter an instruction to the image display control unit 130. Further, the image display control unit 130 has a function of controlling each constituent component.

The image display control unit 130 is connected to the plurality of radiation detecting apparatuses 120, 122, and 124. More specifically, the image display control unit 130 is connected to the plurality of radiation detecting apparatuses 120, 122, and 124 via a wired or wireless network or a dedicated line. Each of the plurality of radiation detecting apparatuses 120, 122, and 124 can capture an image with the radiation generated by the radiation generating unit 112 and can output image data to the image display control unit 130.

The image display control unit 130 is functionally operable as an application that runs on a computer. The image display control unit 130 can control operational states of the plurality of radiation detecting apparatuses 120, 122, and 124 in such a way as to output an image and/or a graphical user interface to the display unit 132.

The image display control unit 130 can control radiation generation timing and imaging conditions for the radiation generating unit 112. Further, the image display control unit 130 can control image data imaging timing and output timing for the plurality of radiation detecting apparatuses 120, 122, and 124. The image display control unit 130 can cause the plurality of radiation detecting apparatuses 120, 122, and 124 to perform imaging operations simultaneously. The image display control unit 130 can cause the plurality of radiation detecting apparatuses 120, 122, and 124 to output image data simultaneously.

The image display control unit 130 has a function of performing noise removal and other image processing on the image data output from the plurality of radiation detecting apparatuses 120, 122, and 124. Further, the image display control unit 130 can perform trimming, rotation, and other image processing on the images output from the plurality of radiation detecting apparatuses 120, 122, and 124. The display unit 132 can display the images output from the image display control unit 130.

The subject 100 stands on a step board of the photography platform 110 so that the subject 100 can be accurately positioned in relation to the plurality of radiation detecting apparatuses 120, 122, and 124 and the radiation generating unit 112. In the present example embodiment, a straight line extending from the radiation generating unit 112 to the center of the second radiation detecting apparatus 122 is perpendicular to the longitudinal (i.e., vertical) direction of the photography platform 110. When the radiation generating unit 112 emits radiation toward the plurality of radiation detecting apparatuses 120, 122, and 124, the radiation transmits through the subject 100 and reach the plurality of radiation detecting apparatuses 120, 122, and 124. Thus, respective radiation detecting apparatuses can detect the radiation. The image display control unit 130 generates a composite image of the subject 100 by composing image data obtained by the plurality of radiation detecting apparatuses 120, 122, and 124. The composite image is a long-sized image that has been acquired through the long-size imaging operation that covers a wide observation region. The display unit 132 displays the long-sized image output from the image display control unit 130.

The radiographing system according to an example embodiment of the present invention can perform a long-size imaging operation capable of taking an image of a spinal cord, an entire lower limb, or the whole body of the subject 100 during a single radioactive ray irradiation operation. The plurality of radiation detecting apparatuses 120, 122, and 124 is simultaneously irradiated with radiation emitted from the radiation generating unit 112 in the irradiation range 114. For example, an operator controls the diaphragm to shield the radiation appropriately or adjusts the distance from the radiation generating unit 112 to the plurality of radiation detecting apparatuses 120, 122, and 124.

As another example embodiment, each of the plurality of radiation detecting apparatuses 120, 122, and 124 can be configured to have a detection function of automatically detecting radiation emitted from the radiation generating unit 112. The automatic detection function of respective radiation detecting apparatuses 120, 122, and 124 includes detecting radiation in response to the emission of the radiation by the radiation generating unit 112 and storing electric charges caused by the radiation. When any one of the radiation detecting apparatuses 120, 122, and 124 detects the emission of the radiation, each of the plurality of radiation detecting apparatuses 120, 122, and 124 starts a reading operation and acquires image data.

Figure 2:
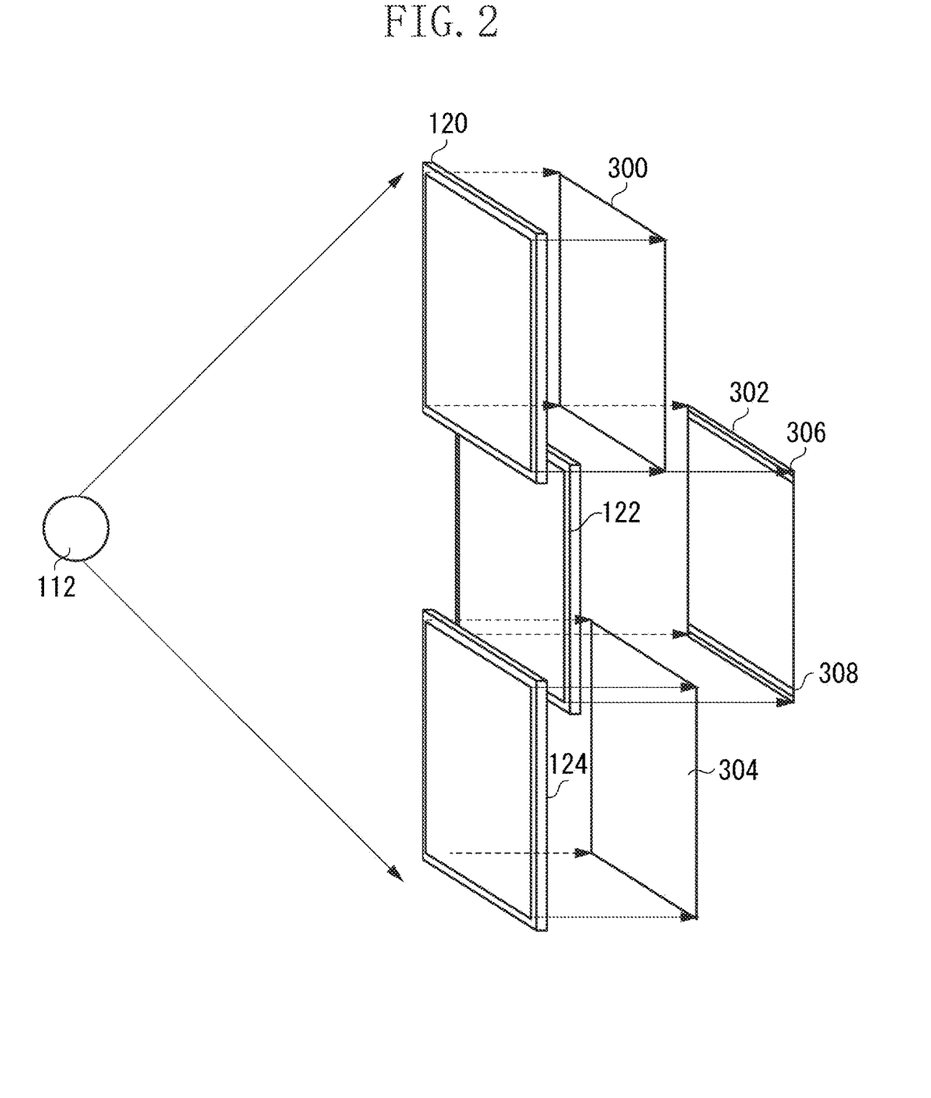
FIG. 2 illustrates defective regions of a long-sized image generated by the radiographing system according to an example embodiment of the present invention.
Figure 4A:
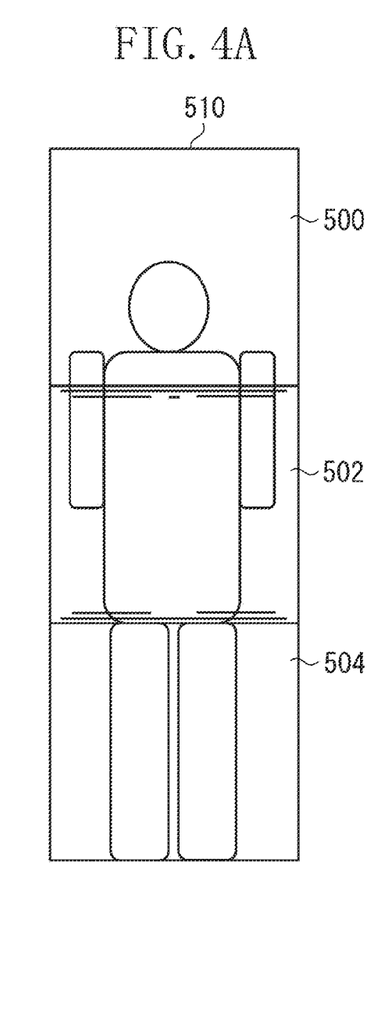
FIGS. 4A, 4B, and 4C illustrate correction processing that can be performed by an image correction unit of the radiographing system according to an example embodiment of the present invention.
Figure 4B:
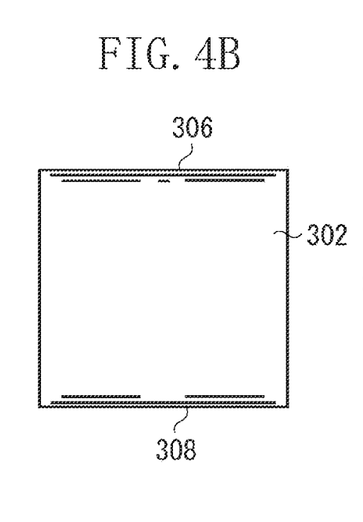
Figure 4C:
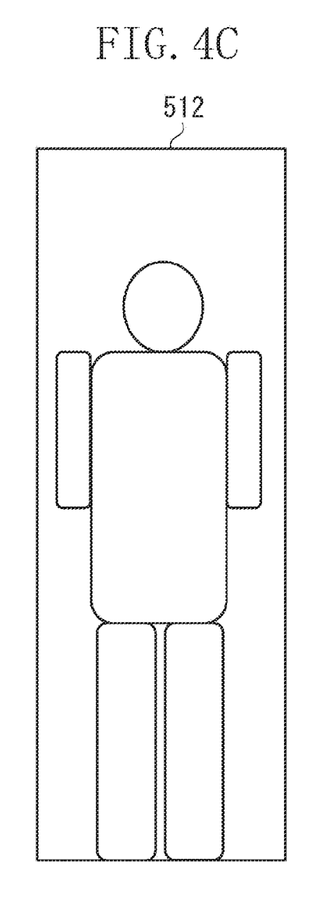

Example image data detectable by the plurality of radiation detecting apparatuses 120, 122, and 124 will be described in detail below with reference to FIG. 2. FIGS. 4A to 4C schematically illustrate an example configuration of the radiographing system according to an example embodiment of the present invention and illustrate an example pattern of image data obtainable by the radiographing system. FIG. 2 illustrates an example alignment pattern of the plurality of radiation detecting apparatuses 120, 122, and 124 that are sequentially arrayed. FIG. 4B includes an example image data 302 acquired from the second radiation detecting apparatus 122 when the radiographing system performs an imaging operation in a state where no subject is present. The image data 302 includes reflections that represent structural information about the radiation detecting apparatuses 120 and 124.

More specifically, the image data 302 acquired from the second radiation detecting apparatus 122 includes a reflection region 306 representing the structural information about an overlapping lower end portion of the first radiation detecting apparatus 120. Further, the image data 302 acquired from the second radiation detecting apparatus 122 includes a reflection region 308 representing the structural information about an overlapping upper end portion of the third radiation detecting apparatus 124.

FIG. 2 illustrates example image data (i.e., a radiographic image) 300 acquired from the first radiation detecting apparatus 120, which does not include any reflection representing structural information about another radiation detecting apparatus. Further, FIG. 2 illustrates example image data (i.e., a radiographic image) 304 acquired from the third radiation detecting apparatus 124, which does not include any reflection representing structural information about another radiation detecting apparatus. Therefore, the image data 302 corresponds to structural data including reflections as position and pixel value information. In this respect, the reflection region 306 and the reflection region 308 can be regarded as examples of the structural information.

Figure 3:
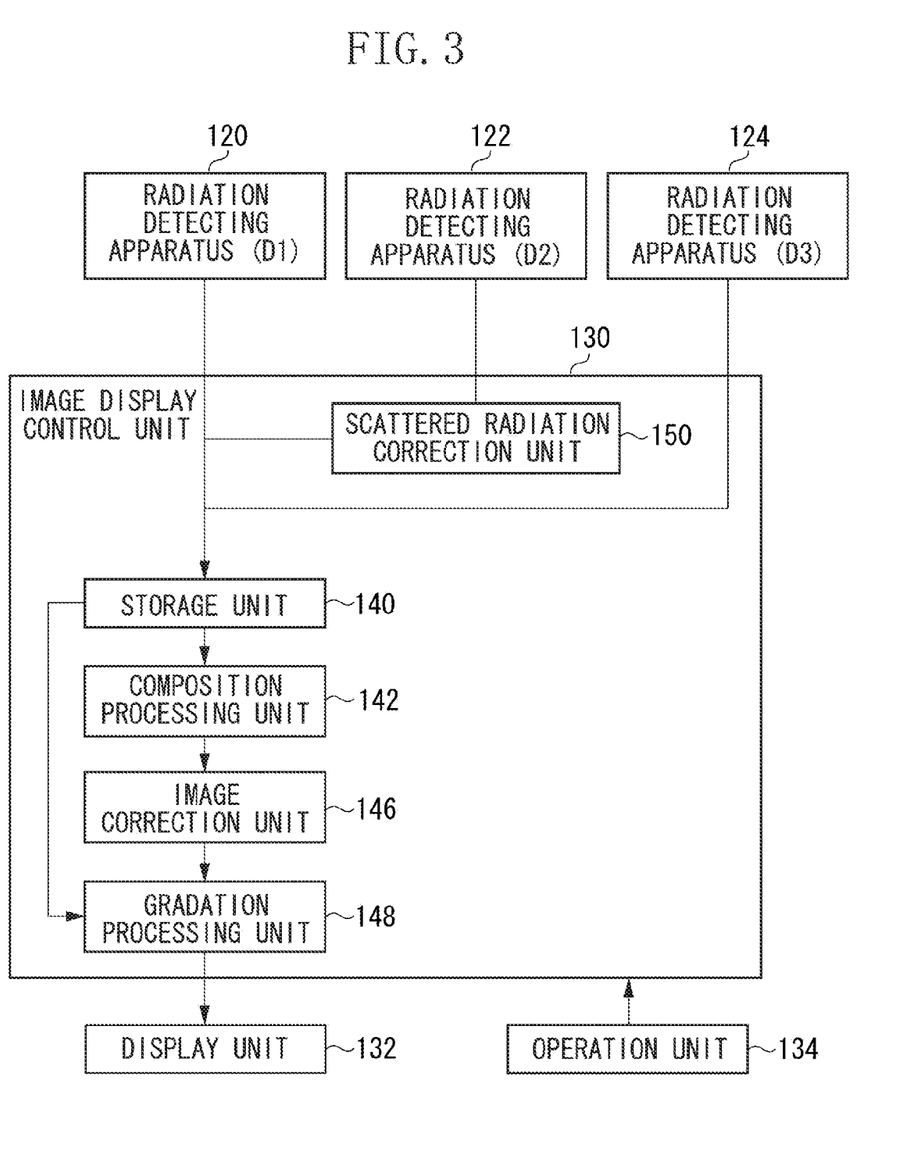
FIG. 3 illustrates a configuration of the radiographing system (mainly, an image display control unit) according to a first example embodiment of the present invention.

FIG. 3 illustrates an example configuration of the radiographing system according to an example embodiment of the present invention. The image display control unit 130 includes a storage unit 140, a composition processing unit 142, an image correction unit 146, a gradation processing unit 148, and a scattered radiation correction unit 150. The storage unit 140 can store image data having been output from each radiation detecting apparatus. The composition processing unit 142 can generate a long-sized image by composing image data obtained from respective radiation detecting apparatuses. The image correction unit 146 can correct the long-sized image generated by the composition processing unit 142 in such a way as to eliminate or reduce a defective region included in the long-sized image. The gradation processing unit 148 can perform gradation processing on the long-sized image corrected by the image correction unit 146. The scattered radiation correction unit 150 can correct (or reduce) scattered radiation for the image data having been output from the second radiation detecting apparatus 122.

As illustrated in FIG. 1, the second radiation detecting apparatus (D2) 122 mainly photographs a chest region and an abdominal region of the subject 100. The chest region and the abdominal region of the subject 100 are representative body parts in which a great amount of scattered radiation may be generated. The second radiation detecting apparatus (D2) 122 can detect radiation having passed through the body parts in which a great amount of scattered radiation has been generated. Therefore, the scattered radiation correction unit 150 performs scattered radiation correction processing on only the image data output from the second radiation detecting apparatus (D2) 122, which is located at the position closest to the chest region or the abdominal region of the subject 100.

More specifically, in the case where the first radiation detecting apparatus (D1) 120, the second radiation detecting apparatus (D2) 122, and the third radiation detecting apparatus (D3) 124 are arrayed in the longitudinal direction of the photography platform 110, the scattered radiation correction unit 150 performs scattered radiation correction processing on the image data output from the second radiation detecting apparatus (D2) 122 that is centrally disposed. In other words, the scattered radiation correction unit 150 performs the scattered radiation correction processing on the image data output from the second radiation detecting apparatus (D2) 122, which is sandwiched between the first radiation detecting apparatus (D1) 120 and the third radiation detecting apparatus (D3) 124.

The scattered radiation correction unit 150 uses the following method in performing the scattered radiation correction processing. The scattered radiation can be approximately modeled by using the primary X ray passing through the subject. The following formula can be used to express a composite image P'(x, y), which is composed of the primary X ray P(x, y) and the scattered radiation S(x, y).

$$P'(x,y)=P(x,y)+S(x,y) \quad \text{[Formula 1]}$$

In general, the scattered radiation S(x, y) can be modeled by using the following formula.

$$S(x,y)=\{-P(x,y)\log P(x,y)\}*[A \exp\{-(x^2+y^2)/(2a^2)\}+B \exp\{-(x^2+y^2)/(2b^2)\}] \quad \text{[Formula 2]}$$

In the above-mentioned formula 2, the sign "*" represents a convolution operator, the term including the coefficient "A" represents a Rayleigh scattering model, and the term including the coefficient "B" represents a Compton scattering model. The scattered radiation correction unit 150 derives the primary X ray P(x, y) from the composite image P'(x, y) according to the formula 1 and the formula 2 in the scattered radiation correction processing.

Further, the scattered radiation correction unit 150 can use a successive approximation method to calculate a primary X-ray image Pg(x, y) that minimizes the following formula.

$$E=|P'(x,y)-P_g'(x,y)|^2 \quad \text{[Formula 3]}$$

In the formula 3, Pg'(x, y) can be expressed by the following formula because the composite image Pg(x, y) has been calculated based on the primary X-ray image Pg(x, y).

$$Pg'(x,y)=Pg(x,y)+Sg(x,y) \quad \text{[Formula 4]}$$

Further, Sg(x, y) can be expressed by the following formula.

$$Sg(x,y)=\{-Pg(x,y)\log Pg(x,y)\}*[A \exp\{-(x2+y2)/(2a2)\}+B \exp\{-(x2+y2)/(2b2)\}]$$

The scattered radiation correction unit 150 can use any other appropriate method that is applicable to the scattered radiation correction processing. For example, the scattered radiation correction unit 150 can estimate a body thickness of the subject by using scattered radiation components obtained by the second radiation detecting apparatus (D2) 122 and can use the estimated body thickness of the subject to correct the scattered radiation for the image data (i.e., the radiographic image).

A head area, arms, and legs of the subject 100 are representative body parts where a relatively smaller amount of scattered radiation may occur. Therefore, the scattered radiation correction unit 150 may not perform the scattered radiation correction for the image data output from the first radiation detecting apparatus (D1) 120 and the third radiation detecting apparatus (D3) 124.

The storage unit 140 stores the image data (i.e., the radiographic images) output from the plurality of radiation detecting apparatuses 120, 122, and 124. As illustrated in FIG. 3, the first radiation detecting apparatus 120 is the radiation detecting apparatus (D1). The second radiation detecting apparatus 122 is the radiation detecting apparatus (D2). The third radiation detecting apparatus 124 is the radiation detecting apparatus (D3).

The storage unit 140 can store the image data output from the radiation detecting apparatuses 120, 122, and 124 together with time information. Accordingly, in storing the image data, the storage unit 140 can refer to the acquired time information about respective radiographic images to check if the radiographic images have been simultaneously acquired from the radiation detecting apparatuses 120, 122, and 124. Further, in storing the image data, the storage unit 140 can discriminate a radiographic image that includes image information about the subject from a radiographic image that does not include any image information about the subject.

Further, the storage unit 140 can store a plurality of radiographic images simultaneously photographed by the plurality of radiation detecting apparatuses 120, 122, and 124 in association with positional information (i.e., spatial alignment information) about respective radiation detecting apparatuses. For example, the storage unit 140 can store the image data output from the first radiation detecting apparatus 120 and the image data output from the second radiation detecting apparatus 122, associating them as adjacent to each other. Similarly, the storage unit 140 can store the image data output from the second radiation detecting apparatus 122 and the image data output from the third radiation detecting apparatus 124, associating them as adjacent to each other. Further, the storage unit 140 can store in association information about the second radiation detecting apparatus 122 that it is disposed on the back side of the radiation detecting apparatuses 120 and 124. The storage unit 140 can output a plurality of pieces of image data and related positional information to the composition processing unit 142.

The composition processing unit 142 generates a long-sized image by composing a plurality of pieces of image data stored in the storage unit 140. In generating the long-sized image in this case, the composition processing unit 142 composes a plurality of pieces of image data that includes image information about the subject 100.

Further, in generating the long-sized image, the composition processing unit 142 refers to the time information and the positional information to compose a plurality of pieces of image data output from the radiation detecting apparatuses 120, 122, and 124. More specifically, the composition processing unit 142 determines a plurality of pieces of image data (i.e., radiographic images) simultaneously output from the radiation detecting apparatuses 120, 122, and 124 as composition targets based on the time information, and composes the plurality of pieces of image data. The composition processing unit 142 determines a positional relationship between a plurality of pieces of image data output from the radiation detecting apparatuses 120, 122, and 124 based on the positional information and composes the plurality of pieces of image data.

For example, according to the example illustrated in FIG. 1, the composition processing unit 142 locates the image data output from the first radiation detecting apparatus 120 at an upper position. The composition processing unit 142 locates the image data output from the third radiation detecting apparatus 124 at a lower position. And, the composition processing unit 142 locates the image data output from the second radiation detecting apparatus 122 at an intermediate position. Further, the composition processing unit 142 takes the positional information into consideration to check the overlapping relationship between respective image data, in performing the composition. For example, the image data output from the second radiation detecting apparatus 122 includes defective regions at upper and lower end regions thereof because the second radiation detecting apparatus 122 is located far from the radiation generating unit 112 compared to the first and second radiation detecting apparatuses 120 and 124 and disposed in such a manner that the second radiation detecting apparatus 122 partly overlaps with another radiation detecting apparatuses 120 and 124. On the other hand, the image data output from each of the first and third radiation detecting apparatuses 120 and 124 does not include any defective region. Therefore, the composition processing unit 142 uses the image data output from the first and third radiation detecting apparatuses 120 and 124 in generating the long-sized image in each boundary region where two neighboring radiation detecting apparatuses overlap with each other. In other words, the composition processing unit 142 selects the image data to be used in the composition in such a way as to minimize the defective regions included in the long-sized image. As mentioned above, the composition processing unit 142 can generate a long-sized image by composing a plurality of pieces of image data that has been acquired by imaging a plurality of neighboring imaging regions.

The image correction unit 146 performs correcting processing on the composite image output from the composition processing unit 142 to eliminate the defective regions. More specifically, the image correction unit 146 corrects each defective region by using structural information representing a structural member of the radiation detecting apparatus and a pixel value distribution of a normal region neighboring the defective region. In other words, the image correction unit 146 corrects each defective region of the long-sized image by using information about the normal image region neighboring the defective region.

In the present example embodiment, the structural information represents each structural member of the radiation detecting apparatus that may be included as a reflection in a radiographic image. The structural information includes various information (e.g., radiation attenuation coefficient, thickness, and position) about each substance that is present in the radiation detecting apparatus. In correcting a defective region of a long-sized image, if there is not any undesirable reflection, it is expected that an edge of the defective region correlates to the pixel value distribution of a spatially neighboring normal region. Accordingly, considering the structural information that causes a reflection, the image correction unit 146 can correct the defective region by performing correction in such a way as to equalize a pixel value distribution of the defective region with the pixel value distribution of the normal region.

For the purpose of simplifying the following description, it is assumed that the radiographing method according to the present example embodiment includes acquiring image data, as structural information, by performing imaging operations with a plurality of radiation detecting apparatuses which overlap with each other in a state where no subject is present, as described in detail below. The structural information can be expressed by the pixel value that represents a reflection caused by a structural member of the radiation detecting apparatus. For example, the pixel value becomes a smaller value if a thick structural member having a greater radiation attenuation coefficient causes a reflection in the pixel and becomes a larger value if a thin structural member having a smaller radiation attenuation coefficient causes a reflection in the pixel.

FIGS. 4A to 4C illustrate example correction processing that can be performed by the image correction unit 146 of the radiographing system according to an example embodiment of the present invention. More specifically, the image correction unit 146 corrects image data including image defective regions that have been caused by the reflections of structural members that constitute the first radiation detecting apparatus 120 and the third radiation detecting apparatus 124.

FIG. 4A illustrates a long-sized image 510 that has been generated by composing a plurality of pieces of image data (radiographic images). The composition processing unit 142 generates the long-sized image 510 and then outputs the long-sized image 510 to the image correction unit 146.

FIG. 4B illustrates an example of the structural information that can be used in the correction processing to be performed by the image correction unit 146. In the present example embodiment, the radiographing system performs an imaging operations in the state where the subject 100 is not present and designates the image data 302 acquired by the second radiation detecting apparatus 122 as structural information.

FIG. 4C illustrates a corrected long-sized image 512 that has been obtained by subtracting the defective regions, which have been caused by the reflections of the structural members that constitute the first radiation detecting apparatus 120 and the third radiation detecting apparatus 124, from the long-sized image 510 illustrated in FIG. 4A. The image correction unit 146 can output the corrected long-sized image 512. Further, an image 500 illustrated in FIG. 4A is image data output from the first radiation detecting apparatus 120. According to the illustrated example, the image 500 mainly includes a head area and shoulders of the subject 100. An image 502 illustrated in FIG. 4A is image data output from the second radiation detecting apparatus 122. According to the illustrated example, the image 502 mainly includes an upper body part and arms of the subject 100. An upper end portion and a lower end portion of the image 502 are defective regions including the reflections of the structural information about the radiation detecting apparatuses 120 and 124. The composition processing unit 142 performs composition processing with reference to an alignment relationship between respective radiation detection portions in such a way as to minimize the area occupied by the defective regions in the long-sized image.

An image 504 illustrated in FIG. 4A is image data output from the third radiation detecting apparatus 124. According to the illustrated example, the image 504 mainly includes legs of the subject 100.

As illustrated in FIG. 4A, the composition processing unit 142 generates the long-sized image 510 by composing the image 500, the image 502, and the image 504. In other words, the composition processing unit 142 can acquire a composite whole-body image of the subject 100.

As illustrated in FIG. 4C, the image correction unit 146 performs correction processing for correcting the long-sized image 510 illustrated in FIG. 4A by removing the defective regions including the reflections of the structural members of the first radiation detecting apparatus 120 and the third radiation detecting apparatus 124. More specifically, the image correction unit 146 generates the corrected long-sized image 512, which does not include the defective regions including the reflections of the structural members of the radiation detecting apparatuses (i.e., a part of the radiation detecting apparatus).

The gradation processing unit 148 performs gradation processing on the long-sized image obtained by composing a plurality of pieces of image data (i.e., radiographic images). More specifically, the gradation processing unit 148 acquires the plurality of pieces of image data, which has been acquired from the radiation detecting apparatuses 120, 122, and 124, from the storage unit 140. The gradation processing unit 148 analyzes feature quantities of the plurality of pieces of image data acquired from the radiation detecting apparatuses 120, 122, and 124 and determines gradation conversion characteristics of the long-sized image in such a way as to effectively use a dynamic range of the display unit 132.

Then, the gradation processing unit 148 converts a gradation of the long-sized image with reference to the determined gradation conversion characteristics. The feature quantities include a histogram of each image data, a maximum pixel value, and a minimum pixel value thereof. The gradation processing unit 148 calculates the feature quantities by performing analysis processing on the plurality of pieces of image data acquired from respective radiation detecting apparatuses 120, 122, and 124.

The gradation processing unit 148 can perform gradation processing on the long-sized image corrected by the image correction unit 146. As mentioned above, the gradation processing unit 148 performs the gradation processing on the long-sized image from which the defective regions have been removed. Therefore, the gradation processing unit 148 can appropriately perform the gradation processing on the long-sized image. More specifically, the gradation processing unit 148 can perform the gradation processing on the long-sized image while reducing adverse influences caused by the reflections of the structural members constituting the first radiation detecting apparatus 120 and the third radiation detecting apparatus 124.

The display unit 132 can display the long-sized image in which the defective regions have been corrected. More specifically, the display unit 132 can improve the image quality of the long-sized image that includes the reflections of the structural members that constitute the radiation detecting apparatuses.

The radiographing system according to the above-mentioned example embodiment of the present invention includes the plurality of radiation detecting apparatuses 120, 122, and 124 that can detect radiation. Further, the radiographing system includes the composition processing unit 142 that can generate a long-sized image by composing a plurality of radiographic images acquired from the plurality of radiation detecting apparatuses. The radiographing system further includes the scattered radiation correction unit 150 that can perform scattered radiation correcting processing for the image data output from the second radiation detecting apparatus 122 (i.e., at least one of the plurality of radiation detecting apparatuses). Accordingly, the radiographing system can improve the image quality of each long-sized image by appropriately correcting the scattered radiation.

Figure 5:
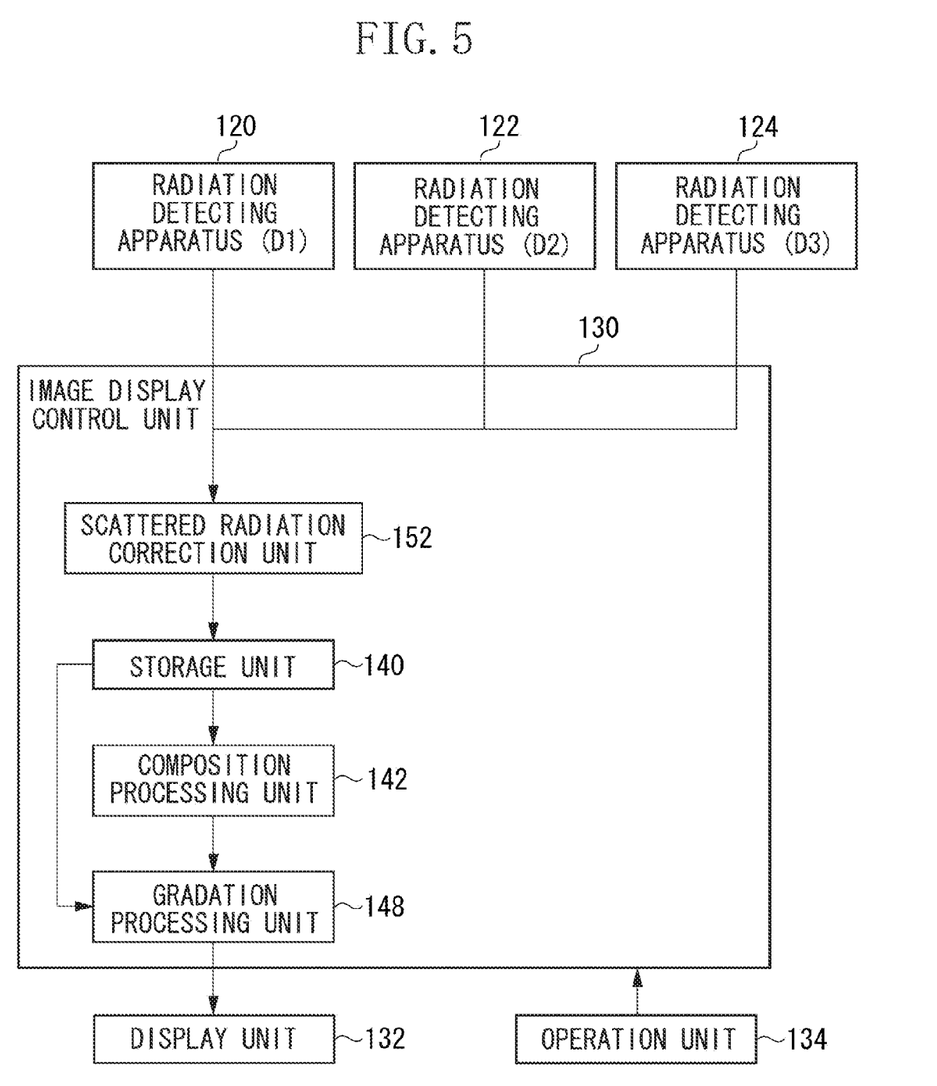
FIG. 5 illustrates a configuration of the radiographing system (mainly, the image display control unit) according to a second example embodiment of the present invention.

Next, a second example embodiment will be described in detail below. The second example embodiment is different from the first example embodiment in that a scattered radiation correction unit 152 is provided to perform scattered radiation correction for the image data output from the plurality of radiation detecting apparatuses 120, 122, and 124.

As illustrated in FIG. 2, the image data 302 acquired from the second radiation detecting apparatus 122 includes the reflection region 306 of the structural information about the overlapping lower end portion of the first radiation detecting apparatus 120. Further, the image data 302 acquired from the second radiation detecting apparatus 122 includes the reflection region 308 of the structural information about the overlapping upper end portion of the third radiation detecting apparatus 124.

The scattered radiation correction unit 152 corrects the scattered radiation for the defective regions of a long-sized image (i.e., the reflection region 306 and the reflection region 308 of the image data 302) in a region where neighboring radiation detecting apparatuses overlap with each other, with reference to the structural information representing the structural members of the radiation detecting apparatuses. The structural information represents each structural member of the radiation detecting apparatus that may cause a reflection in a radiographic image. The structural information includes characteristic data (e.g., radiation attenuation coefficient, thickness, and position) about a substance that is present in the radiation detecting apparatus.

The reflection region 306 and the reflection region 308 are regions influenced by the scattered radiation in the first radiation detecting apparatus 120 and the third radiation detecting apparatus 124. More specifically, the scattered radiation occurs in proportion to the thickness (i.e., the structural member) of each of the first radiation detecting apparatus 120 and the third radiation detecting apparatus 124. The scattered radiation correction unit 152 performs scattered radiation correction for the image data that constitutes a long-sized image by referring to the thickness of each of the first radiation detecting apparatus 120 and the third radiation detecting apparatus 124, or by referring to the thickness of a substance that is present in each of the first radiation detecting apparatus 120 and the third radiation detecting apparatus 124. More specifically, the scattered radiation correction unit 150 corrects the scattered radiation for the image data in each defective region in which neighboring radiation detecting apparatuses overlap with each other with reference to the body thickness of a subject, and the thickness of each of the first radiation detecting apparatus 120 and the third radiation detecting apparatus 124, or the thickness of the substance that is present in each of the first radiation detecting apparatus 120 and the third radiation detecting apparatus 124.

Further, the scattered radiation correction unit 152 can enhance the degree of the scattered radiation correction in each of the reflection region 306 and the reflection region 308 of the image data 302. In this case, the scattered radiation correction unit 152 can lower the degree of the scattered radiation correction in a region other than the reflection region 306 and the reflection region 308 of the image data 302.

Further, the scattered radiation correction unit 152 can perform the scattered radiation correction for the image data output from the plurality of radiation detecting apparatuses 120, 122, and 124, in such a way as to prevent the image quality of a measurement target body part of the subject from being adversely influenced. The measurement target body part is, for example, a spine of the subject. The scattered radiation correction unit 152 extracts the spine of the subject from the image data that constitutes the long-sized image. Then, the scattered radiation correction unit 152 corrects the scattered radiation for the image data that constitutes the long-sized image in such a manner that the pixel value range of the spine of the subject remains within a predetermined range.

Further, the operation unit 134 designates a predetermined body part. The predetermined body part designated in this case can be determined beforehand. The predetermined body part is a radiographing target body part to be photographed in association with a clipping condition indicating the size of the region to be extracted from the radiographic image.

If the operation unit 134 designates the predetermined body part, the scattered radiation correction unit 152 can extract the region including the predetermined body part (e.g., a chest region and an abdominal region) from the image data that constitutes the long-sized image. If the imaging target body part is positioned on the front side of the subject, the scattered radiation correction unit 152 can recognize right and left ends and upper and lower ends in the predetermined body part of the subject with reference to edge information about the image data.

For example, if the operation unit 134 designates the chest region, the scattered radiation correction unit 152 can extract the chest region from the image data that constitutes the long-sized image. If the operation unit 134 designates the abdominal region, the scattered radiation correction unit 152 can extract the abdominal region from the image data that constitutes the long-sized image.

Further, the scattered radiation correction unit 152 can set the degree of correcting the scattered radiation included in the radiation based on the predetermined body part. If the processing target region includes the predetermined region (e.g. the chest region and the abdominal region), the scattered radiation correction unit 152 enhances the degree of the scattered radiation correction. If the processing target region does not include the predetermined region (e.g., the chest region and the abdominal region), the scattered radiation correction unit 152 lowers the degree of the scattered radiation correction.

As mentioned above, the scattered radiation correction unit 152 corrects the scattered radiation for the region including the predetermined body part (e.g., the chest region and the abdominal region) extracted from the image data that constitutes the long-sized image. On the other, the scattered radiation correction unit 152 does not correct the scattered radiation for a region that does not include the predetermined body part (e.g., the chest region and the abdominal region) in the image data that constitutes the long-sized image.

Further, the scattered radiation correction unit 152 may select the image data output from the second radiation detecting apparatus (D2) 122 disposed at the position closest to the chest region or the abdominal region of the subject and perform the scattered radiation correction processing on the selected image data. In this case, the scattered radiation correction unit 152 does not select the image data output from the first radiation detecting apparatus (D1) 120 and the third radiation detecting apparatus (D3) 124 positioned adjacently to the head area, the arms, and the legs of the subject 100 and does not perform the scattered radiation correction processing on the non-selected image data.

Figure 6:
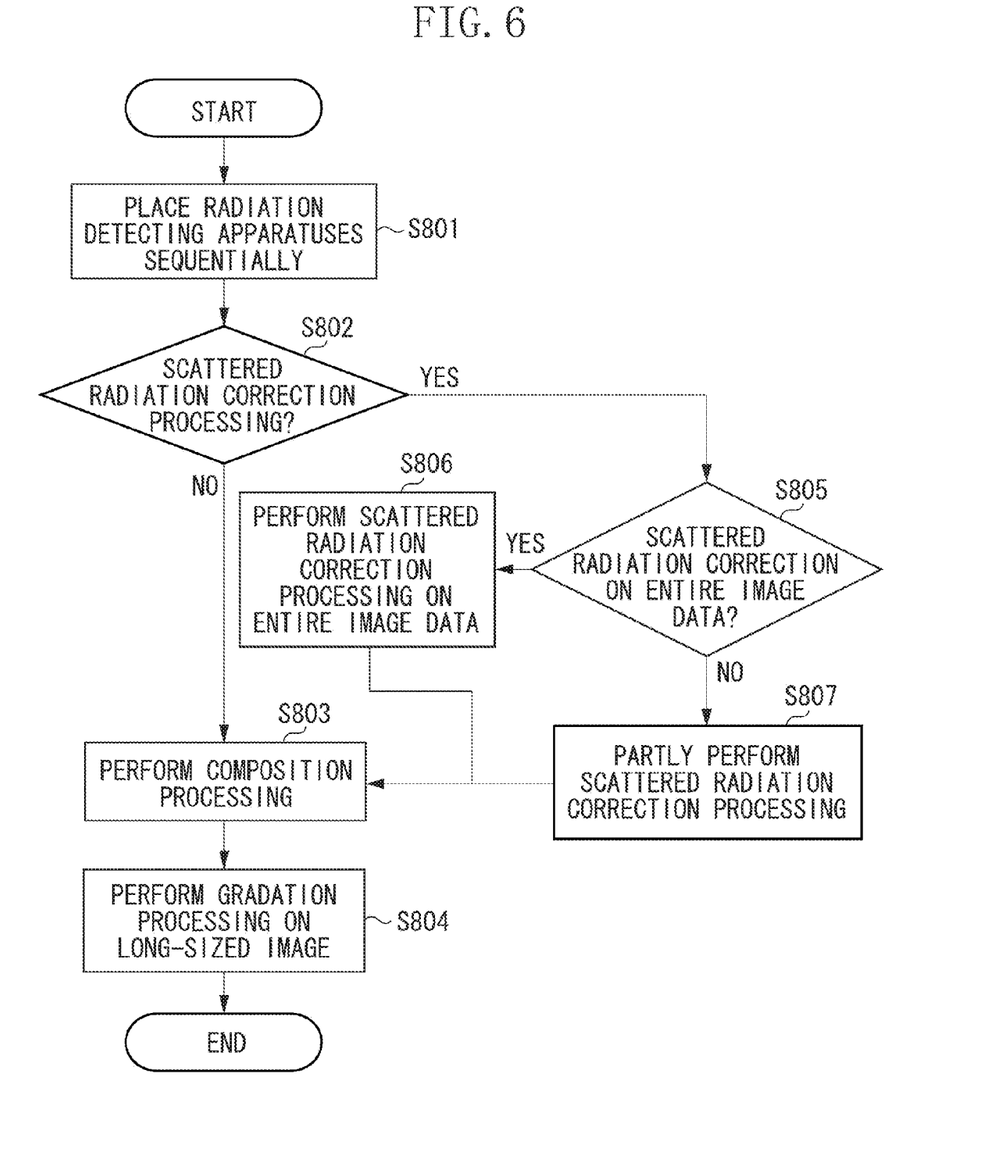
FIG. 6 is a flowchart illustrating an operation procedure according to the second example embodiment of the present invention.

Next, an example operation procedure according to the second example embodiment will be described in detail below with reference to a flowchart illustrated in FIG. 6.

In step S801, an operator places a plurality of radiation detecting apparatuses on the photography platform 110. More specifically, the operator arrays the radiation detecting apparatuses 120, 122, and 124 sequentially in the longitudinal direction of the photography platform 110. In this case, the operator places the plurality of radiation detecting apparatuses in such a way as to cause neighboring radiation detecting apparatuses to overlap partly so that effective pixel regions capable of detecting radiation overlap with each other.

In step S802, the operator determines whether to perform scattered radiation correction processing on image data output from the radiation detecting apparatuses 120, 122, and 124. If the operator does not perform the scattered radiation correction processing (No in step S802), the operation proceeds to step S803. If the operator performs the scattered radiation correction processing (Yes in step S802), the operation proceeds to step S805.

In step S803, the composition processing unit 142 generates a long-sized image by composing the image data output from the radiation detecting apparatuses 120, 122, and 124. In this case, the image correction unit 146 can perform additional processing on the long-sized image output from the composition processing unit 142 in such a way as to reduce defective regions including reflections of structural members of the first radiation detecting apparatus 120 and the third radiation detecting apparatus 124.

In step S804, the gradation processing unit 148 performs gradation processing on the long-sized image output from the composition processing unit 142. Alternatively, the gradation processing unit 148 can perform gradation processing on the long-sized image corrected by the image correction unit 146.

In step S805, the operator determines whether to perform the scattered radiation correction processing on the entire image data output from the radiation detecting apparatuses 120, 122, and 124. If the operator does not perform the scattered radiation correction processing on the entire image data (No in step S805), the operation proceeds to step S807. If the operator performs the scattered radiation correction processing on the entire image data (Yes in step S805), the operation proceeds to step S806.

In step S806, the scattered radiation correction unit 152 uniformly performs the scattered radiation correction processing on the entire image data output from the radiation detecting apparatuses 120, 122, and 124.

In step S807, the scattered radiation correction unit 152 partly performs the scattered radiation correction processing on the image data output from the radiation detecting apparatuses 120, 122, and 124. For example, as described above, the scattered radiation correction unit 152 corrects the scattered radiation for the image data output from the second radiation detecting apparatus 122, which includes the defective regions (i.e., the reflection region 306 and the reflection region 308) due to the overlapping relationship between the radiation detecting apparatuses, with reference to the structural information representing the structural members of the radiation detecting apparatuses.

The scattered radiation correction unit 152 may select any one of the radiation detecting apparatuses 120, 122, and 124 and perform the scattered radiation correction processing on a radiographic image (i.e., image data) output from the selected radiation detecting apparatus. In other words, the scattered radiation correction unit 152 does not perform the scattered radiation correction for any radiographic image output from the non-selected radiation detecting apparatus. More specifically, if the operator selects any one of the radiation detecting apparatuses 120, 122, and 124 via the operation unit 134, the scattered radiation correction unit 152 performs the scattered radiation correction processing on the selected radiation detecting apparatus. In the present example embodiment, the scattered radiation correction unit 152 can perform the scattered radiation correction processing on a radiographic image acquired from one radiation detecting apparatus selected from the plurality of radiation detecting apparatuses.

Further, the scattered radiation correction unit 152 can select two radiation detecting apparatuses from the radiation detecting apparatuses 120, 122, and 124 and perform the scattered radiation correction processing on the radiographic images output from the selected radiation detecting apparatuses.

As mentioned above, the scattered radiation correction unit 152 corrects the scattered radiation for each of the image data output from the plurality of radiation detecting apparatuses 120, 122, and 124. Therefore, the scattered radiation correction unit 152 can appropriately correct the scattered radiation and improve the image quality of a long-sized image.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to example embodiments, it is to be understood that the invention is not limited to the disclosed example embodiments. The scope of the following claims is to be accorded the broadest interpretation so as to encompass all such modifications and equivalent structures and functions.

This application claims the benefit of Japanese Patent Application No. 2016-080646, filed Apr. 13, 2016, which is hereby incorporated by reference herein in its entirety.

What is claimed is:
1. A radiographing system comprising:
   a plurality of radiation detecting apparatuses that can detect radiation and output radiographic images, the plurality of radiation detecting apparatuses being provided to overlap with one another;

a scattered radiation correction unit configured to perform reduction processing of a scattered radiation component in a defective region of at least one of the output radiographic images, the defective region including a structure of one or more of the radiation detection apparatus;

a composition processing unit configured to generate a long-sized image on a basis of the radiographic images acquired from the plurality of radiation detecting apparatuses; and an image correction unit configured to perform correction processing on the defective region in the long-sized image, thereby reducing the structure of the radiation detecting apparatus in the long-sized image using a pixel value of an image region other than the defective region.

2. The radiographing system according to claim 1, wherein if the plurality of radiation detection apparatuses is arrayed in a longitudinal direction of a photography platform, the scattered radiation correction unit reduces the scattered radiation component from a radiographic image output from a radiation detecting apparatus centrally positioned among the plurality of radiation detecting apparatuses.

3. The radiographing system according to claim 1, wherein if the plurality of radiation detection apparatuses is arrayed in a longitudinal direction of a photography platform, the scattered radiation correction unit reduces the scattered radiation component from a radiographic image output from a radiation detecting apparatus sandwiched between two radiation detecting apparatus among the plurality of radiation detecting apparatuses.

4. The radiographing system according to claim 1, wherein the scattered radiation correction unit reduces the scattered radiation component from a radiographic image output from a radiation detecting apparatus positioned closest to a chest region or an abdominal region of a subject.

5. The radiographing system according to claim 1, wherein the scattered radiation correction unit reduces the scattered radiation component in a region where the radiation detecting apparatuses overlap with each other, with reference to structural information about structural members of respective radiation detecting apparatuses.

6. The radiographing system according to claim 1, wherein, with respect to at least one of a body thickness direction of a subject and a thickness direction of the radiation detecting apparatus, the scattered radiation correction unit reduces the scattered radiation component from a radiographic image in a region where the radiation detecting apparatuses overlap with each other.

7. The radiographing system according to claim 1, wherein the scattered radiation correction unit reduces the scattered radiation component from the radiographic images output from the plurality of radiation detecting apparatuses to prevent deterioration of an image of a measurement target body part of a subject.

8. The radiographing system according to claim 1, wherein, with respect to a predetermined body part, the scattered radiation correction unit sets a degree of correction for scattered radiation included in radiation received by at least one of the radiation detecting apparatuses among the plurality of radiation detecting apparatuses.

9. The radiographing system according to claim 1, wherein the scattered radiation correction unit selects any one of the radiation detecting apparatuses among the plurality of radiation detecting apparatuses and reduces the scattered radiation component from a radiographic image output from the selected radiation detecting apparatus.

10. A radiographing system comprising
a plurality of radiation detecting apparatuses that can detect radiation and output radiographic images, the plurality of radiation detecting apparatuses being provided to overlap with one another; and
a composition processing unit configured to generate a long-sized image on a basis of the plurality of radiographic images acquired from the plurality of radiation detecting apparatuses,
wherein a reduction processing is performed to reduce a scattered radiation component of a defective region including a structure of one or more of the radiation detection apparatus and a correction processing is performed on the defective region in the long sized image using a pixel value of an image region other than the defective region.

11. A radiographing method for generating a long-sized image, the radiographing method comprising:
producing a corrected radiographic image by performing reduction processing of a scattered radiation component of a defective region where the radiation detecting apparatus overlap and performing correction processing on the defective region in the long-sized image using a pixel value of an image region other than the defective region; and
producing a composite radiographic image by composing the corrected radiographic image with a plurality of radiographic images acquired from the plurality of radiation detecting apparatuses.

12. A radiographing method for generating a long-sized image by composing a plurality of radiographic images acquired from a plurality of radiation detecting apparatuses, wherein the method includes
performing reduction processing of a scattered radiation component of a defective region including a structure of one or more of the radiation detection apparatus, where the one or more of the radiation detecting apparatuses overlap with each other, in the long-sized image; and
performing correction processing on the defective region in the long-sized image using a pixel value of an image region other than the defective region.

* * * * *